(12) United States Patent
Torossian

(10) Patent No.: US 6,806,253 B2
(45) Date of Patent: Oct. 19, 2004

(54) IMMUNODULATORY COMPLEX AND USE THEREOF IN HELICOBACTER DISEASES

(76) Inventor: Fernand Narbey Torossian, 10 rue Noël Ballay, 31400 Toulouse (FR)

(*) Notice: Subject to any disclaimer, the term of this patent is extended or adjusted under 35 U.S.C. 154(b) by 0 days.

(21) Appl. No.: 09/125,747
(22) PCT Filed: Feb. 25, 1997
(86) PCT No.: PCT/FR97/00334
§ 371 (c)(1), (2), (4) Date: Aug. 25, 1998
(87) PCT Pub. No.: WO97/30716
PCT Pub. Date: Aug. 28, 1997

(65) Prior Publication Data
US 2002/0032152 A1 Mar. 14, 2002

(30) Foreign Application Priority Data
Feb. 26, 1996 (FR) .............................. 96 02445

(51) Int. Cl.$^7$ ..................... A61K 38/00; A61K 39/395; A61K 45/00; A61K 39/38; G01N 33/554
(52) U.S. Cl. ................... 514/12; 424/180.1; 424/184.1; 424/190.1; 424/193.1; 424/203.1; 424/234.1; 424/282.1; 435/7.32; 530/323
(58) Field of Search ......................... 514/12; 424/180.1, 424/184.1, 190.1, 193.1, 203.1, 234.1, 282.1; 435/7.32; 530/323

(56) References Cited

U.S. PATENT DOCUMENTS 4,460,575 A    7/1984   d'Hinterland

OTHER PUBLICATIONS

Rappuoli et al Development of a vaccine against Helicobacter pylori : a short overview, European Journal of Gastroenterology and Hepatology, vol. 5, (suppl. 2) pp. 576–578, 1993.*

Yokota et al. "Low Antigenicity of the Polysaccharide Region of Helicobacter pylori" Infection and Immunity vol. 65, No. 9, pp. 3509–3512, 1997.*

HP World–Wide, a publication from Brocades Pharma BV Leiderdorp, The Netherlands, Feb. 1992.*

Buck et al. "Relation of Campylobacter pyloridis to Gastric and Peptic Ulcer", The Journal of Infectious Diseases, vol. 153, No. 4, pp. 664–669, 1986.*

U.S. patent application Ser. No. 08/347,322, Torossian, filed Jan. 30, 1995.

Use of Bacterial Ribosomal Immunostimulators in Respiratory Tract.

* cited by examiner

Primary Examiner—Rodney P Swartz
Assistant Examiner—Khatol S Shahnan-Shah
(74) Attorney, Agent, or Firm—John A. Artz; Artz & Artz, P.C.

(57) ABSTRACT

A therapeutical vaccine complex having activity specific for Helicobacter bacteria as well as non-specific immunomodulation activity for regulating the natural defenses of the body. The drug is also useful for preventing relapses, particularly in cases of resistance to conventional treatment. The drug essentially consists of RNA, selective membrane fractions of microbial germs, particular amino acid sequences, sodium chloride and a steroidal anti-inflammatory in predetermined proportions enabling simultaneous delivery of antibiotics and frenosecretories. Said drug is particularly suitable for treating digestive tract diseases caused by Helicobacter (antral gastritis, duodenal ulcers, gastric ulcers, oesophagitis, hepatitis) and preventing stomach cancer and degenerative infectious MALT (mucosa-associated lymphoid tissue) lymphoma, as well as coronary diseases directly or indirectly dependent on Helicobacter infections.

10 Claims, No Drawings

IMMUNODULATORY COMPLEX AND USE THEREOF IN *HELICOBACTER* DISEASES

TECHNICAL FIELD OF THE INVENTION

The present invention relates to a therapeutic and preventive anti-bacterial vaccine complex which possesses a vaccinating power linked to the presence of specific antigens against *Helicobacter pylori* (previously called *Campylobacter pylori*), *Helicobacter hepaticus, Helicobacter coronari*, and nonspecific antigens providing immunomodulation.

BACKGROUND OF THE INVENTION (MARSHALL B. J., WARREN Jr., Unidentified curved *bacilli* in the stomach of the patients with gastritis and peptic ulceration *Lancer* 1984: i:1311–4)).

(MÉGRAUD F., *Helicobacter pylori*, the most important bacterium among the mucus bacteria. *La letter de l'infectiologue* 1993; 8 (suppl. 4): 151–9).

It is well known, in bacteriology, that the surface antigens of the walls, membranes or capsules (combined or free in soluble form in the culture medium) are of a glycoprotein, polypeptide or polysaccharide nature.

Vaccines combining associative factors, such as membrane proteoglycan or polysaccharide substances, extracted from pathogenic microbes, with ribonucleic acid of ribosomal origin (RNA) can be used in the production of acellular vaccines (cf. Inf. and Immunity, 1, 574–82, 1970 and PCT WO 94/22462).

These vaccines use specific antigens corresponding to specifically determined microbial diseases.

However, the antigenicity is essentially linked to the level of RNA (of the ribosomes in particular) in microbial cells, inter alia. Immunocompetent cells (ICC) directly use these RNAs as active carriers.

SUMMARY OF THE INVENTION

To produce the complex of the invention, with the *Helicobacter* bacterial serotype antigen, we coupled preferably by means of covalent bonds, RNA, preferably of ribosomal origin, with an amino acid sequence of glycoprotein nature, preferably present in type III collagen. In humans, collagen represents approximately a third of the proteins in the body. The type III was chosen for its amino acid sequence and its presence in the dermis, the vascular wall and the digestive epithelial mucous membranes.

In our complex, we have used, as stabilizer, cell membrane fractions derived from the same microbes as those which served for the production of the ribosomal RNA. These membrane fractions contain all of the peptidoglycan substances and are known, in addition, as immunity adjuvants.

It is, in addition to *Helicobacter pylori, hepaticus* and *coronari*, useful to have—glucopolysaccharide or proteoglycan—membrane fractions derived from various microbial organisms which have served to provide the RNA by extraction of their ribosomes, which microbes are known for their immunogenesis (recruitment of macrophages, activation of T lymphocytes, potentiation of the synthesis of immunoglobulins, secretory IgA's in particular (11 S), increase in phagocytosis and stimulation of dependent T cells and the like).

This was thus thought of because, in the precise case of the pathogenesis induced by *Helicobacter pylori, hepaticus* or *helmannii, coronari*, the body must produce, in addition to the specific humoral immune response, a cellular response in order to make up for the inefficacy of the antibodies in protecting the individual.

It is known that cell-mediated response does not give rise to the production of antibodies, but only to the generation of sensitized lymphoid cells specific for the antigen involved.

The T lymphocytes act by themselves and/or through the cytokines, and either an inflammatory type response or a cytotoxic response is observed.

The pathogenic power of *Helicobacter* lies in its ability to colonize the gastric mucous membrane, to survive in the gastric juice and to multiply therein in spite of the host's immune response, and to generate lesions which are sometimes irreversible (adenocarcinoma, gastric lymphoma or MALT "mucous associated lymphoid tissue" lymphomas), (PARSONNET J: *Helicobacter pylori* and gastric cancer. Gastroenterol Clin North Am 1993, 22:89–104.

WORTHERSPOON A. C., DOGLIONI C., DISS T. C. et al.: Regression of primary low-grade B-cell gastric lymphoma of mucosa associated lymphoid tissue type after eradication of *Helicobacter pylori*. Lancet 1993; 342:575–7.

MOHANDAS, *Helicobacter pylori* and lymphoma, N Eng J Med 1994: 331:746–7).
when it is insufficient during injection: resistance to phagocytosis, induction of apoptosis and the like.

(PETERSON P. K., VERHOEF J., SCHMELING D. & QUIE P. G.: Kinetics of phagocytosis and bacterial killing by human polymorphonuclear leucocytes and monocytes, J. Infec. Dis. 136:502–509, 1977.

KIEHLBAUCH J. A., ALBACH R. A., BAUM I. K., CHANG K. P. Phagocytosis of *Campylobacter jejuni* and its intracellular survival in mononuclear phagocytes, Infect Immun 1985; 48:446–51).

DETAILED DESCRIPTION OF THE INVENTION

Constituents of the Vaccine Complex Which is the Subject of the Invention

The complex of the invention comprises dual molecules constituted by the coupling of a functional amino acid arm, ensuring binding to a target, with a genetic RNA arm corresponding to the coded description of the composition of the functional arm.

A—The RNAs of ribosomal origin which can be used may be extracted from the strains chosen from the following group, this list not being limitative:

*Helicobacter pylori* (or *Campylobacter*), *hepaticus, coronari* . . .

*Klebsiella pneumoniae*

*Streptococcus* (*pneumoniae* and *pyogenes*)

*Staphylococcus aureus*

*Serratia marcescens*

*Escherichia coli*

*Salmonella typhimurium*

*Corynebacterium* (*granulosum, paryum,* acnes)

*Mycobacterium* (*tuberculosis, smegmatis, chelonei*)

*Haemophilus influenzae*

*Pneumococcus* type II

*Rothia dentocariosus*

*Bacterium coli*

*Shigella dysentariae*

*Enterococcus*

Nocardia (*asteroides, brasiliensis, rhodocrans, opaca, rubra*)
Calmette-Guerin bacillus,
or from a mixture thereof.

The average molecular weights of these RNAs are between 5104 and 108 Dalton.

Many industrial processes exist for the preparation of RNA. We will cite as an example the process for extracting RNA described in Infect. and Immunity, 1. 574–82. 1970; the bacteria are ground and then subjected to fractional precipitation, the ribosomal proteins are solubilized, the RNA precipitated is treated with Pronase and, finally, purified by ion-exchange chromatography.

If the RNA is obtained by enzymatic route, the final purification may be carried out by molecular sieve chromatography. See in particular on this subject:

C. EHRESMAN (1972)—Biochimie, 54, 901
H. KAGAWA (1972)—J. Biochem., (1972), 827
M. SANTER (1973)—J. Bact., 116, 1304
NOMURA (1974)—Ribosomes—Ed. Cold Spring Harbor Laboratory.

B—The membrane fractions of bacterial cells which can be used may be extracted from the following strains, the lists given not being limitative:

1—For capsular polysaccharides
a. *Helicobacter pylori* and *hepaticus*
b. *Klebsiella pneumoniae*
c. *Streptococcus pneumoniae*
d. *Hemophilus influenzae*
e. *Escherichia coli*
a. *Helicobacter pylori, hepaticus* and *coronari*

(HILLS B. A., Gastric mucosal barrier: evidence for *Helicobacter pylori* ingesting gastric surfacant and deriving protection from it. Gut. 1983 May: 34(5): 588–93.

GENTA R. M., ROBASON G O, GRAHAM D. Y., Simultaneous visualization of *Helicobacter pylori* and gastric morphology; a new strain. Human Pathology; 1994 Mar. 25 (3); 221–6.

MAJEWSKI S. I., and C. S. GOODWIN, 1988, Restriction endonuclease analysis of the genome of *Campylobacter pylori* with a rapid extraction method: evidence for considerable genomic variation. J. Infect. Dis. 157; 465–471.

GEIS G., LEYING H., SUERBAUM S., MAI U. & OPFERKUCH W.: Ultrastructure and chemical analysis of *Campylobacter pylori* flagella. J. Clin. Microbial, 27; 436–441, 1989).

b. *Kiebsiella pneumoniae*
(C. ERBING, L. KENNE, B. LINBERG, J. LONNOREN (1976)—Structural studies of the capsular polysaccharide of *Kiebsiella pneumoniae* type I (Carbohydr. Res., 50 (1976) 115–20).

W. NIMMICH (1968) Zur isolierung und qualitativen Bausteinanalyse der K. Antigen von Klebsiellen (Isolation of the *Klebsiella* K antigen and qualitative analysis of its structural components) (Med. Mikrobio and Immunol., 154, 117, 131).

C. RICHARD (1973)—Etudc antigenique et biochemique de 500 souches de *Kiebsiella* (Antigenic and biochemical study of 500 *Klebsiella* strains) (Ann. Biol. Clin., 1973)).

c. *Streptoccus pneumoniae:*
(F. KAUFFMANN and E. LUND (1954) (Int. Bull, Bact. Nomencl. 4, 125–28).

FELTON and OTTINGER (J. of Bacteriology, 1942, 43, 94, 105)

M. COLIN, M. D. MAC LEOD et al., Prevention of pneumococcal *pneumoniae* by immunization with specific capsular polysaccharides (J. Exp. Med, 1945, 82, 445–65).

A. R. DOCHEZ and O. T. AVERY—The elaboration of specific soluble substance by *Pneumococcus* during growth (1971) (J. Exp. Med. 26, 477–93).

WEST PHAL and LUDERITZ (1952) (Z. Naturf. 7B, 148).

C. P. J. GLAUDEMANS and H. P. TREFFERS—An improved preparation of the capsular polysaccharide from *Diplococcus pneumoniae* (Carbohydr. Res. 1967, 4, 181–84)).

d. *Hemophilus influenzae* (capsular polysaccharide polyribosephosphate type)

(P. ANDERSON et al. (1972)—Immunization of humans with polyribosephosphate, the capsular antigen of *Hemophilus influenzae* type B (J. of Clin. Invest. vol. 51, 1972, 39–44).

P. ANDERSON et al. (1977)—Isolation of the capsular polysaccharide from supernatant of *Hemophilus influenzae* type B (Infect. And Immun., 1977, 15 (2), 472–77)).

e. *Escherichia coil* (capsular polysaccharides) (LUDERITZ et al. (1977)—Somatic and capsular antigens of gram-negative bacteria (Compr. Biochem. 26 A, 105–228).

BOYER H. W. and D. ROULLAND-DISSOIX, (1969)—A complementation analysis of the restriction and modification in *Escherichia coli*, J. Mol. Biol. (41:459–472).

CASADABAN, M. and S. N. COHEN (1980)—Analysis of gene control signals by DNA fusion and cloning in *E. coli*, J. Mol. Biol. (138; 179–207).

LUGTENBERG B., J. Meijers, R. Peters, P. van der Hock and L. van Alphen (1975)—Electrophoretic resolution of the "major outer membrane protein" of *Escherichia coil* K12 into four bands. (FEBS Lett. 58; 254–258)).

2—For the membrane lipopolysaccharides (LPS)—
*Corynebacterium* (*avidum, bovis, diphteriae, enzymicum, equi, fascians, flaccum, faciens, flavidum, fustiforme, granulosum, helvolum, hypertrophicans, insidiosum, liquefaciens, paryum, paurometabolum, pyogenes, tumescens, xerosis*)

*Helicobacter pylori*, hepaticus, coronari
*Kiebsiella* (*pneumoniae* and *rhinoscleromatis*)
*Salmonella typhimurium*
*Serratia* (*marcescens, corralina, indica, plymuthica, kiluea*)
*Neisseria meningitidis*
*Escherichia coli*

(GOODWIN C. S. "*Helicobacter Pylori:* $10^{th}$ anniversary of its culture in April 1982". (Gut 1993: 34: 293–4).

C. ERBIN et al. (1977)—Structural studies on the *Klebsiella* LPS (Carbohydr. Res., 56, 377–81).

C. B. CASTOR et al. (1971)—Characteristics of a highly purified pyrogenic LPS of *Klebsiella pneumoniae* (J. of Pharm. Sci. 60, (10), 1578–80).

K. FUKUSHI (1964)—Extraction and purification of endotoxin from *Enterobacteriaceae:* a comparison of selected methods and sources (J. of Bacteriol. 87, (2), 391–400).

G. A. LIMJUCO—Studies on the chemical composition of LPS from *Neisseria meningitidis* group B (J. of Gen. Microbiol. 1978, 104, 187–91).

G. A. ADAMS (1967)—Extraction of LPS from gram-negative bacteria with DMSO (Canad. J. Biochem., 45, 422–26).

K. G. JOHNSON (1976)—Improved techniques for the preparation of bacterial LPS (Canad. J. Microbiol. (22), 29–34).

Y. B. KIM et al. (1967)—Biologically active endotoxins from *Salmonella* mutans (J. of Bacteriol., 94, (5), 1320–261)).

3—For the Membrane Proteins

*Helicobacter pylori*

*Escherichia coli*

*Serratia marcescens*

*Streptococcus pyogenes*

*Salmonella typhimurium.*

*Helicobacter pylori, Hepaticus, coronari*

GOBERT (B.), LABIGNE (A.), de KORWIN (J. D.), CONROY (M. C.), BENE (M. C.), FAURE (G. C.)—Polymerase chain reaction for *Helicobacter pylori*, (Rev. Esp. Enf Digest, 1980, 78 (suppl 1), 4.

TOWBIN, H., T. STAEHELIN and J. GORDON, 1979. Electrophoretic transfer of proteins from polyacrylamide gels to nitrocellulose sheets; procedure and some applications. Proc. Natl. Acad. Sci. USA 76:4350–4354.

*Escherichia coli*

S. F. STIRM et al. (1967)—Episome, carried surface antigen K 88 of *Escherichia coli* (J. of Bactgeriol., 93, (2), 731–39).

S. J. BETZ et al. (1977)—Chemical and biological properties of a protein rich fraction of bacterial LPS (J. of Immunol., 119 (4), 1475–81).

*Serratia marcescens*

W. WOBER (1971)—Studies on the protein moiety of endotoxin from gram-negative bacteria, characterisation of the protein-moiety isolated by acetic acid hydrolysis of endotoxin of *Serratia marcescens* (Eur. J. Biochem., 19:3 pp. 357–67).

*Streptococcus pyogenes*

M. K. WITTNER (1977)—Homologous and heterologous protection of mice with group-A *Streptococcal* M protein vaccine (Infect. and Immun., 1977, 15, (1), 104–8).

*Salmonella thyphimurium*

N. KUUSI et al. (1979)—Immunization with major outer mebrane protein in experimental *salmonellosis* of mice (Infect. and Immun., 1979, 25, (3), 857–62).

C. BARBER et al. (1972)—The protective role of proteins from *Salmonella thyphimurium* in infection of mice with their natural pathogen (Rev. Immunol., 36, 77–81).

G. DELORD (1979)—Etude d'un antigène vaccinant contenu dans le surnageant de culture de *Salmonella thyphimurium*, souche M-206. [Study of a vaccinating antigen contained in the culture supernatant of *Salmonella thyphimurium* strain M-206] Medical thesis in Lyon No. 428, 1979.

G. W. GOODMAN (1979)—Characterization of the chemical and physical properties of a novel B-lymphocyte activator endotoxin protein (Infect. and Immun., 1979, 24(3), 685–96).

4—For the Teichoic and Lipoteichoic Acids

*Streptococci, staphylococci* and *lactobacilli* (the surface of gram-positive bacteria is made of teichoic acid, which is a glycerol polymer, linked by phosphodiester bridges).

The following articles describe the methods of production:

M. M. BURGER (1966)—Teichoic acids: antigenic determinants, chain separation and their location in the cell wall (Microbiology 56, 910–17).

K. W. KNOX (1973)—Immunological properties of teichoic acids (Bacteriol. Reviews, 37, 21, 215–57).

G. A. MILLER (1976)—Effects of *Streptococcal lipoteichoic* acid on host response in mice (Infect. and Immun., 1976, 13, (5), 1408–17).

A. J. WICKEN et al. (1975)—Lipoteichoic acids: a new class of bacterial antigens (Science, 187, 1161–67).

Various Assays Possible

RNA

FISKE and SUBBAROW—Assay of phosphorus. HPLC chromatography on an ion-exchange column for qualitative control (J. Biol. Chem. (1926), 66, 375).

Proteins

LOWRY (J. Biol. Chem. (1951), 193, 265–75).

Hexoses

T. A. SCOTT—Colorimetric assay using anthrone (Anal. Chem. (1953). 25, 1956–61).

Hexosamines

L. A. ELSON (Biochem. J (1953), 27, 1824–28).

Lipopolysaccharides

J. JANDA and E. WORK (Febs Letters, 1971, 16(4), 343–45).

C—The other immunity adjuvant factors, in addition to the membrane fractions, are collagen type III sodium chloride The collagen type III used is characterized by the following amino acid concentrations expressed in g/kg:

| a - Amino acid sequences similar to the following sequence (the concentrations are expressed in g/kg): | | |
|---|---|---|
| aspartic acid | AA | 51.5 |
| hydroxyproline | HP | 107.0 |
| threonine | TH | 16.1 |
| serine | SE | 27.8 |
| glutamic acid | GA | 95.9 |
| proline | PR | 124.0 |
| glycine | GL | 149.0 |
| alanine | AL | 87.9 |
| valine | VA | 23.3 |
| methionine | ME | 7.5 |
| isoleucine | IL | 14.4 |
| leucine | LE | 27.8 |
| tyrosine | TY | 6.7 |
| phenylaline | PA | 14.4 |
| lysine | LY | 28.6 |
| histidine | HI | 5.5 |
| arginine | AR | 73.0 |
| b - The following standard analysis: | | |
| colour | | yellowish white |
| apparent density | | 250 g/l |
| moisture | | 6% |
| pH of a 10% solution | | 6.9 |
| Engler viscosity at 40° C. (17.75% solution) | | 2.5 |
| fat content | | 0.9% |
| ash content | | 2.2% |
| content of Fe + Cu + Ca | | 462 mg/kg |
| heavy metals | | not detectable by arc emission spectrography |
| elemental analysis | C | 46.80% |
| | H | 7.10% |
| | N | 14.96% |

The composition of the vaccine complex which is the subject of the invention, combining ribosomal RNAs or RNA fragments, membrane fractions (for example proteoglycans from *Klebsiella pneumoniae*) and collagen type III, supplemented with sodium chloride and an anti-inflammatory agent, makes it possible, by administration of low doses causing no toxicity, to obtain a high level of protection and of cure.

The preferred presentation is the injectable form of the composition presented above, but it is possible to use other presentations and/or other areas or additives compatible with a medical use.

Mechanism of Action of the Vaccine Complex

This therapeutic (vaccine) complex may be assimilated to a specific vaccine (through an "inert system" which is intended to increase the immunogenicity of a recombinant subunit vaccine and of vaccines consisting of peptides), and a nonspecific vaccine with the characteristics of a lymphokine, which, by attaching to the macrophages, plays an essential role in the immune response towards *Helicobacter* (KAZI J. I., SINNIAH R., JAFFRAY N. A., ALAM S. M., ZAMAN V., ZUBERI S. J. & KAZI A. M.: Cellular and humoral immune response in *Campylobacter pylori*-associated chronic gastritis, J. Pathol. 159; 23 1–237, 1989).

Since 1974–75 (A. S. and G. P. YOUMANS), it has been observed that the effect of inhibition of the immune response to RNA was provided by various inhibitors, (J. Immunol., 112, pp. 271–284, 1974).

YOUMANS had worked on a single bacterial strain (*Mycobacterium tuberculosis*), whose "parasitism" is solely intracellular, (YOUMANS A. S. and G. P., 1975, The immune system and infectious diseases, 1 vol., pp. 399–410).

VENNEMAN et al. have thought since 1972 that the real antigen could be associated with RNA, whose role could be that of an adjuvant, (Infections and Immunity, 5(3), pp. 268–282, 1972). They vaccinated mice with ribosomal RNA, extracted with phenol at 65° C. from ribosomes of a strain of *Salmonella typhimurium*. Thirty days after this vaccination, it was found that the animals were better protected than with an (attenuated) live strain vaccine.

It was in particular observed that the level of protection depended on the quantity of RNA injected.

For example: the ribosomal RNA extracted from *Streptococcus pneumoniae* induces protection of a humoral nature and the ribosomal RNA extracted from *Klebsiella pneumoniae* induces protection of a cellular nature.

(TRIEU-CUOT, P., G. GERBAUD. T. LAMBERT and P. COURVALIN (1985)—In viva transfer of genetic information between gram-positive and gram-negative bacteria. (EMBO J. 4:3583–3587).

This mixture, when injected in vivo into mice and guinea pigs, exerts an action on the alveolar macrophages.

This "transient" effect is determined by assaying the acid phosphatase in the direct haemolysis plaques in contact with mouse spleen cells.

The treatment with our therapeutic and vaccine complex is, for its part, followed by a cellular and humoral immunostimulant effect, with a significant specific and nonspecific action on *Helicobacter pylori*. It is the patient's own body which is stirred into action to "reject the infected cells". A cure is obtained by the action of the PMNs (Polymorphonuclear leukocytes) and of the moncytes simultaneously stirred into action.

(ANDERSEN L. P.; NIELSEN H. Survival and ultrastructural changes of *Helicobacter pylori* after phagocytosis by human polymorphonuclear leukocytes and monocytes. APMIS: 1993 January: 101(1); 61–72).

(STEIGBIGEL R. T. LAMBERT L. H. & REMINGTON J. S.; Phagocytic and bactericidal properties of normal human monocytes, J. Clim. Invest. 53; 131–142, 1974).

(YAM L. T., Li C. Y. & CROSBY W. H.; Cytochemical identification of monocytes and granulocytes, Am. J. Clin. Pathol. 55; 283–290. 1971).

This therapeutic mechanism therefore makes it possible to produce a natural cloning by virtue of the (nonspecific bacterial ribosomal) RNAs opsonized by the adjuvant developed (combination of membrane proteoglycans, of collagen type III and of sodium chloride).

This cloning induces vaccination against the idiotypes of the antibodies, as well as the production of antibodies against the site for attachment of the bacteria. To reduce or inhibit the inflammatory reaction, it is necessary to use, during treatments with the vaccine complex, corticoids (Betamethasone type, for example) in the form of disodium phosphate, at a dose of 20 to 60 mg, by the I.V. or I.M. route.

This action is also accompanied by production of endogenous interferon as well as an activation of the NK cells.

The aim of our immunomodulatory vaccine complex is therefore to induce a local and general immune response which has the effect of preventing or at least of reducing (down to a possible self-defence threshold) the proliferation of an infectious agent introduced into the body.

PRUUL H., LEE P. C., GOODWIN C. S. & MAC-DONALD P. J.—Interaction of *Campylobacter pyloridis* with human immune defence mechanisms, (J. Med. Microbiol. 23; 233–238, 1987).

RATHBONE B. J., WYATT J. I., WORSLEY B. W., SHIRES S. E., TREJDOSIEWICZ L. K., HEATLEY R. V. & LOSOWSKY M. S.—Systemic and local antibody response to gastric *Campylobacter pyloridis* in non-ulcer dyspepsia, (Gut. 27; 642–647, 1986).

STACEY A. R., HAWTIN P. R. & NEWELL D. G.—Local immune responses to *Helicobacter pylori* injections. In: Malgertheimer P. & Ditschuneit H. (Eds.): *Helicobacter pylori*, Gastritis and Peptic Ulcer, (Springer Verlag, Berlin-Heidelberg, 1990, pp. 162–166).

Our therapeutic innovation consists, inter alia, in moderating or eliminating the existence of "suppressive cells" exerting a proinfectious action, in causing an anti-ulcerous reaction by a defensive cellular and/or humoral response; it is the therapeutic response to the problem detected since 1993 by Kist et al.

(KIST M; SPIEGELHALDER C.; MORIKI T.; SCHAEFER H. E.—Interaction of *Helicobacter pylori* (strain 151) and *Campylobacter coli* with human peripheral polymorphonuclear granulocytes), and in preventing infectious recidivations (Zentralbi Bakferoil., 280 (1–2), pp. 58–72, (1993).

BORODY T., ANDREWS P., MANCUSO N., JANKIEWICZ E., BRANDL S.—*Helicobacter pylori* reinfection 4 years post-eradication; (Lancet 1992, 339–1295).

BELL G. D., POWELL K. U., BURRIDGE S. M., HARRISON G., RAMEH B., WEIL J. et al.—Reinfection or recudescence after apparently successful eradication of *Helicobacter pylori* infection: Implications for treatment of patients with duodenal ulcer disease, (Q.J. Med 1993, 86; 375–382).

In conclusion, our therapeutic complex acts by directed evolution, producing RNA molecules which block the *Helicobacter pylori* infection and increase the immunodefence.

(SUERBAUM S., C. JOSENNANS, and A. LABIGNE (1993)—Cloning and genetic characterization of the *Helicobacter pylori* and *Helicobacter mustelae* flaB flagellin genes and construction of *H. pylori* flaA—and flab-negative mutants by electroporarion-inediated allelic exchange. (J. Bacterial. 175:3278–3288).

HAAS R., T. F. MEYER, and J. P. VAN PUTTEN (1993)—Aflagellated mutants of *Helicobacter pylori* generated by genetic transformation of naturally competent strains using transposon shuttle mutagenesis. (Mol. Microbiol. 8:753–760)

CHEN M. LEE A., HAZELL S., HU P., LI Y.—Protective immunisation against *Helicobacter:* the need for stimulation of common mucosal immune system (abstract). (Gastroenterology 1993, 104 (suppl): A681).

It was, moreover, observed during the various clinical trials which were carried out, that the complex of the invention could be successfully substituted for conventional treatments, using in particular triple therapy, in notorious cases of bacterial resistance.

Techniques for Administering the Vaccine Complex

The vaccine complex may be administered orally or parenterally:
either by direct intravenous injection
or by slow infusion
or by subcutaneous injection
or by the transdermal route (per 24 h)
These various techniques have been tried successfully.

The daily doses and their frequency depend largely on the patient's condition. There is no risk of an overdose given the non-toxicity of the complex.

By the intravenous route sequences of one week per month may be used, each day of the week of treatment comprising a slow infusion of 500 ml of a solution containing:

0.9% sodium chloride
40 μg of membrane saccharide fractions (*Klebsiella pneumoniae* proteoglycans)
30 μg of (ribosomal) RNA from:

| | |
|---|---|
| * *Helicobacter pylori* | 7 μg |
| * *Diplococcus pneumoniae* | 7 μg |
| * *Streptococcus pyogenes* (A 12) | 7 μg |
| * *Klebsiella pneumoniae* | 7 μg |
| * *Hemophilus influenzae* | 2 μg |

10 μg of collagen type III described above
8 mg of Betamethasone disodium phosphate (that is to say 2 ml of injectable solution).

This treatment by slow I.V. infusion may be replaced by a treatment by subcutaneous injections on patients who can be followed on an ambulatory basis, each injection containing:

40 μg of membrane saccharide fractions (*Klebsiella pneumoniae* proteoglycans)
30 μg of (ribosomal) RNA from:

| | |
|---|---|
| * *Helicobacter pylori* | 7 μg |
| * *Diplococcus pneumoniae* | 7 μg |
| * *Streptococcus pyogenes* (A 12) | 7 μg |
| * *Klebsiella pneumoniae* | 7 μg |
| * *Hemophilus influenzae* | 2 μg |

10 μg of collagen type III described above
0.5 ml of sodium chloride at 0.9%
4 mg of Betamethasone disodium phosphate (that is to say 1 ml of injectable solution).
This treatment may be continued for several weeks.

By the Oral Route:
using tablets,
2 tablets per day, in a single dose in the morning on an empty stomach, each tablet containing:
400 μg of membrane saccharide fractions (*Klebsiella pneumoniae* proteoglycans)
300 μg of (ribosomal) RNA from:

| | |
|---|---|
| * *Helicobacter pylori* | 70 μg |
| * *Diplococcus pneumoniae* | 70 μg |
| * *Streptococcus pyogenes* (A 12) | 70 μg |
| * *Klebsiella pneumoniae* | 70 μg |
| * *Hemophilus influenzae* | 20 μg |

100 μg of collagen type III described above
2 mg of Betamethasone disodium phosphate.
This treatment can be provided at the rate of 2 tablets per day for one month, followed by booster periods of two tablets per day, one week per month for 3 months.

By the Transdermal Route

Adhesive transdermal therapeutic sytem composed of a reservoir and a permeable membrane providing continuous passage of the active ingredients across the skin and into the bloodstream at a constant rate.

The device should be stuck to a healthy skin surface which is dry and not very hairy (side wall of the abdomen or of the thorax for example).

It comprises:
adhesive polymer
carrier for the adhesive: polyethylene
silicone polyester protective filter Its content is the content of one tablet, and its dosage is identical to the oral route (at the rate of one "patch" for 2 daily tablets).

The following non-limiting examples are given to illustrate the concrete results for our therapeutic vaccine complex.

EXAMPLE 1

Mr. Robert G., 64 years old, was hospitalized following epigastralgia, pyrosis and abdominal pain associated with a transit disorder with alternating diarrhoea—constipation. Digestive endoscopy showed a gastrooesophageal reflux pathology by the opening of the cardia, causing an oesophagitis and a peptic ulcer of the lower oesophagus.

Biopsies were performed, as well as a rapid urease test. The latter, as well as anatomopathology and culture, confirmed the presence of *Helicobacter pylori*.

Conventional treatment (antisecretory and two antibiotics) was prescribed. The tritherapy did not lead to a clinical cure.

Six weeks after the end of the treatment, verification of eradication by the $^{13}$C-labelled urea breath test led to conclusion on the proliferation of bacteria because of its positive nature.

The treatment with the vaccine complex which is the subject of the invention was then carried out in the form of subcutaneous injections.

A month later, clinical cure was observed and the carbon-13-labelled urea breath test was negative.

Six months later, another verification by the $^{13}$C-labelled urea breath test and a verification endoscopy showed an established cure.

For one year, the cure has been definitive.

EXAMPLE 2

Mr. Serge Y., 48 years old, had a type B antral gastritis. Treatment with immunomodulatory complex (the only previous treatments were gastric dressings) in IV form. Clinical cure was obtained fifteen days after the therapeutic sequence. The verifications ($^{13}$C-labelled urea breath test) have been negative for one year.

EXAMPLE 3

Mr. Pierre K. had a duodenal ulcer confirmed by endoscopy (+biopsy, urease test, ELISA tests).

Treatment by the oral route was then introduced. Three weeks later, clinical cure was obtained.

Six weeks later, verification by the $^{13}$C-labelled urea breath test confirmed the eradication.

Six months later, no recidivation was recorded, and the Elisa test showed a nonsignificant (<50%) antibody level.

EXAMPLE 4

Mrs. Sarah L. had a duodenal ulcer associated with a type B gastritis.

The presence of gastric cancer was detected among her brothers and sisters. A full check-up was carried out to show the positive nature of all the tests by an invasive method: culture, histology, amplification of the viral genome (PCR), urea test.

Treatment by the intravenous route over one week and then by subcutaneous boosters over six months was then introduced.

Given the high familial risk, an endoscopy with biopsy was performed from the third month: PCR, cytology, culture, CLO test, were negative.

At the sixth month, a breath test ($^{13}$C) confirmed clinical cure.

What is claimed is:

1. An immunomodulatory complex comprising:
   (a) ribosomal ribonucleic acid extracted from bacteria selected from the group consisting of: *Helicobacter pylori, Helicobacter hepaticus, Helicobacter coronari*, or a mixture thereof;
   (b) the amino acids of the type III collagen; and
   (c) bacterial membrane fractions containing glycopeptides and/or lipopolysaccharides.

2. The immunomodulatory complex according to claim 1 wherein the type III collagen comprises amino acids selected from the group consisting of aspartic acid, hydroxyproline, threonine, serine, glutamic acid, proline, glycine, alanine, valine, methionine, isoleucine, leucine, tyrosine, phenylalanine, lysine, histidine, arginine, and mixtures thereof.

3. The immunomodulatory complex according to claim 1 for use in the treatment of diseases caused by *Helicobacter* bacteria, by the production of antibodies and the production of endogenous interferon.

4. The immunomodulatory complex according to claim 2 for use in the treatment of diseases caused by *Helicobacter* bacteria, by the production of antibodies and the production of endogenous interferon.

5. The immunomodulatory complex according to claim 1, for use against antibiotic-resistant *Helicobacter* bacteria resistant to conventional treatments.

6. The immunomodulatory complex according to claim 2, for use against antibiotic-resistant *Helicobacter* bacteria resistant to conventional treatments.

7. The immunomodulatory complex according to claim 1 wherein the said complex is formulated in such a way that it enables simultaneous administration of the said complex together with substances selected from the group consisting of corticosteroids, antibiotics, antisecretory agents such as proton pump inhibitors, products with bacteriostatic effect, products with bactericidal effect and products with anti-inflammatory effect.

8. The immunomodulatory complex according to claim 2 wherein the said complex is formulated in such a way that it enables simultaneous administration of the said complex together with substances selected from the group consisting of corticosteroids, antibiotics, antisecretory agents such as proton pump inhibitors, products with bacteriostatic effect, products with bactericidal effect and products with anti-inflammatory effect.

9. The immunomodulatory complex according to claim 7 wherein the said complex is formulated in such a way that it enables administration of the said complex by a route selected from intravenous route, subcutaneaous route, transdermal route and per os.

10. The immunomodulatory complex according to claim 8 wherein the said complex is formulated in such a way that it enables administration of the said complex by a route selected from intravenous route, subcutaneaous route, transdermal route and per os.

* * * * *